United States Patent [19]

Coulombe

[11] Patent Number: 4,961,500

[45] Date of Patent: Oct. 9, 1990

[54] MEDICAL DISPENSER TRAY

[76] Inventor: Maurice Coulombe, 4296 Place Charles-Bédard, Charlesbourg, Quebec, Canada, G1H 5L9

[21] Appl. No.: 452,056

[22] Filed: Dec. 18, 1989

[51] Int. Cl.$^5$ .................. A61B 17/06; B65D 1/36; B65D 83/04

[52] U.S. Cl. .................. 206/366; 206/526; 206/562; 206/540; 206/232; 206/561

[58] Field of Search .............. 206/557, 561, 562, 563, 206/538, 526, 540, 366, 365, 232

[56] References Cited

U.S. PATENT DOCUMENTS

| | | | |
|---|---|---|---|
| 3,133,635 | 5/1964 | Gordon et al. | 206/366 |
| 3,207,302 | 9/1965 | Hobbs | 206/366 |
| 3,627,122 | 12/1971 | Garbe, Jr. | 206/366 X |
| 3,727,749 | 4/1973 | Martin | 206/366 |
| 4,034,080 | 8/1977 | Cappuccilli | 206/561 X |
| 4,658,957 | 4/1987 | Guth et al. | 206/366 X |
| 4,767,008 | 8/1988 | Warnecke et al. | 206/366 X |
| 4,844,249 | 7/1989 | Coulombe | 206/365 X |
| 4,863,451 | 9/1989 | Marder | 206/366 X |

FOREIGN PATENT DOCUMENTS 811135 8/1951 Fed. Rep. of Germany ...... 206/366

Primary Examiner—William I. Price

[57] ABSTRACT

A tray adapted to dispense medical treatments and to allow safe transportation and handling of syringes. This medical dispenser tray is characterized by being an improvement over a patented tray providing pairs of holes to safely handle syringes. The present improvement includes an inner tray having elongated recesses each with a hole to allow safe and unmixed transportation of syringes and having indents spaced along its peripheral edge in alignment with the pairs of holes respectively to allow unhampered use of the pairs of aligned holes.

6 Claims, 2 Drawing Sheets

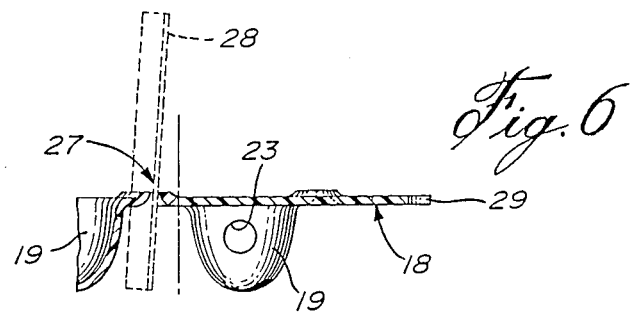
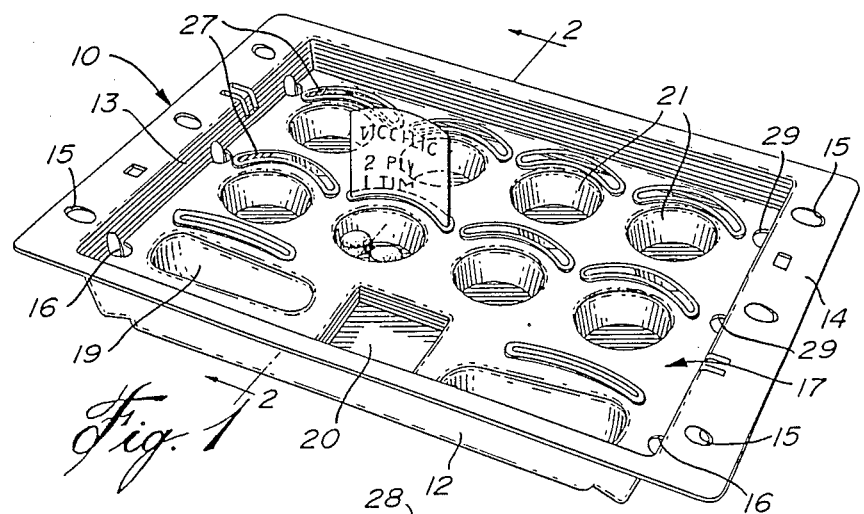
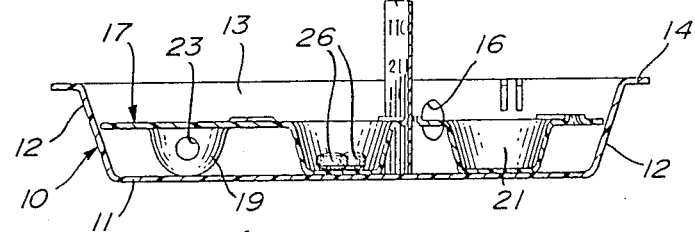

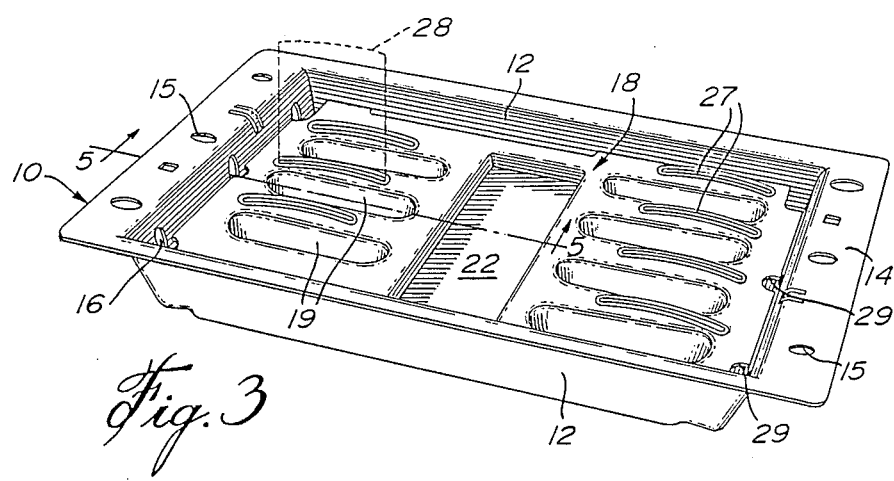
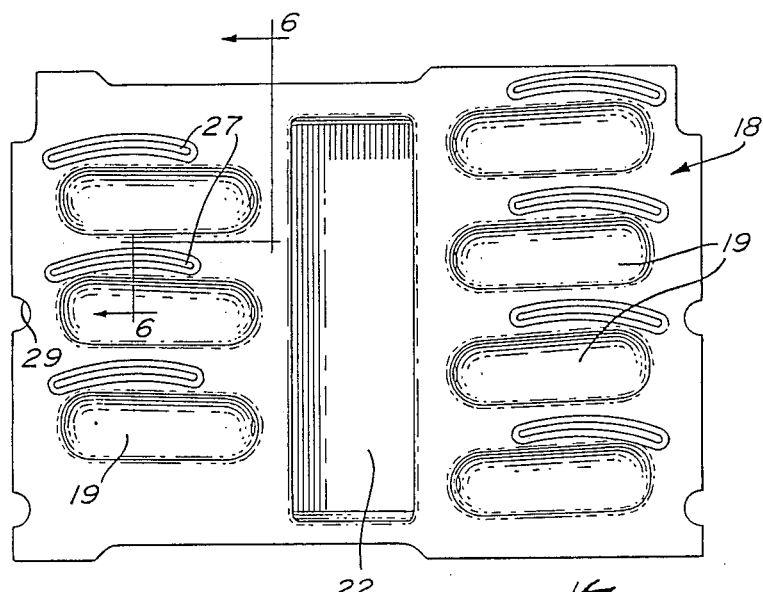
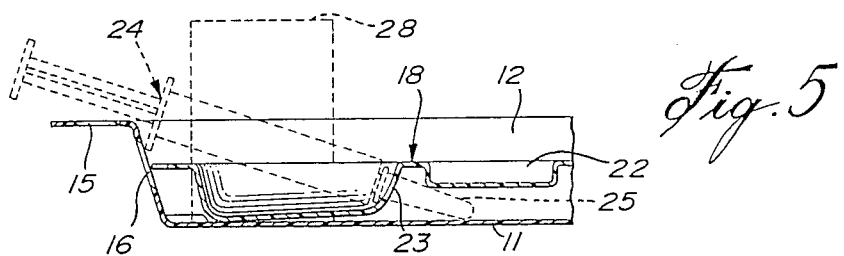

MEDICAL DISPENSER TRAY

BACKGROUND OF THE INVENTION

This invention relates to trays and, more particularly, to a tray of the type adapted to safely transport and handle syringes and pills such as in an hospital.

The safe handling of syringes has been a problem for some time. More recently, even the safe disposal of syringes become a concern. Various solutions to those problems have been proposed. The safe handling of syringes recently became of even bigger concern to control and even prevent the outbreak of epidemic diseases and to prevent injuries to the users, such as to the nurses and doctors. The present invention recognizes that safe handling must also include safe transportation and must also prevent mixing of syringes.

In the U.S. Pat. No. 4,844,249 to the same inventor, there has been proposed a medical supplies container to safely cap and uncap the needles of various types of syringes. In the medical dispenser trays or the like that were proposed so far to handle or transport syringes, the latter are not satisfactorily restrained. They may easily slide or fall off and/or their needles are not safely protected.

The present invention is directed to minimizing the difficulty and danger in handling needles and syringes, including during their transportation. More particularly, the present invention is directed to providing a medical dispenser tray that allows safe handling of the syringes and needles thereof and that allows safe transportation of the syringes.

BRIEF SUMMARY OF THE INVENTION

According to the present invention, the medical dispenser tray includes an outer container having a bottom and side walls cooperatively forming a shallow cavity, a peripheral flange around the side walls, pairs or holes through the flange and side walls to allow uncapping and capping of the needles of syringes. The medical dispenser tray is characterized by an inner tray made of a sheet molded with elongated recesses each with a hole to restrain syringes in them, a utility recess, and selectively also cup-shaped recesses for pills. The sheet forming the inner tray is provided with indents along its edge each aligned with a pair of aligned holes and the deprssed recesses operatively rest on the bottom of the outer container, such that the inner tray and the syringes in the elongated recesses are laterally confined in the shallow cavity by the side walls.

BRIEF DESCRIPTION OF THE DRAWINGS

FIG. 1 is a perspective view of a medical dispenser tray according to a first embodiment of the present invention;

FIG. 2 is a cross-sectional view as seen along line 2—2 in FIG. 1;

FIG. 3 is a perspective view of a medical dispenser tray according to a second embodiment of the present invention;

FIG. 4 is a plan view of the inner tray in the embodiment of FIG. 3;

FIG. 5 is a partial cross-section view as seen along line 5—5 in FIG. 3; and

FIG. 6 is a partial cross-section view as seen along line 6—6 in FIG. 4.

DETAILED DESCRIPTION OF THE DRAWINGS

As best shown in FIGS. 1, 2, and 3, the illustrated medical dispenser tray according to the present invention includes an outer container 10, which in itself is conceived to constitute a medical supplies container as fully shown and described in the U.S. Pat. No. 4,844,249, issued to the same inventor on July 4, 1989. Reference should be made to that patent for a complete understanding of the details of construction of the outer container 10. The latter will however be described to some extent to fully understand the combination constituting the present invention.

The outer container 10 comprises a bottom 11 and pairs of laterally-opposite side walls 12 and 13 cooperatively forming a shallow cavity. A peripheral flange 14 extends around the side walls 12 and 13. The flange 14 and the side walls 13 are provided with holes or apertures of different types to safely cap and uncap the needles of different types of syringes, as defined in details in the above-mentioned patent. In particular, pairs of holes 15 and 16 are spaced along the flange 14 and the opposite side walls 13. Each pair of holes includes a hole 15 in the flange aligned downwardly inward with a hole 16 in the corresponding side wall 13 and constructed and arranged as defined in the U.S. Pat. No. 4,844,249, to receive the capped needle or cap of a syringe to safely cap or uncap the needle without handling the cap during the operation.

In the embodiment of FIGS. 1 and 2, an inner tray 17 and in the embodiment of FIGS. 3, 4, 5, and 6, an inner tray 18 extends in the shallow cavity substantially coextensive with the side walls 12 and 13. The inner trays 17 and 18 are made of a sheet of plastic material, each molded with depressions. The depressions of the inner tray 17 form a pair of elongated recesses 19, a utility recess 20, and eight cup-shaped recesses 21. The depressions of the inner tray 18 form seven elongated recesses 19 and a relatively longer utility tray 22. The depressions forming the recesses 19 and 21 rest on the bottom of the outer container 10 to support the inner tray 17 or 18 in the shallow cavity inside the side walls 12 and 13. Each elongated recess 19 has a hole 23 in its end that is farther from the nearest side wall 13. As can be seen, the elongated recesses 19 are positioned in two transverse rows and are separated by the utility tray 20 or 22 that transversely extends coextensive with the corresponding rows defined by the elongated recesses. Thus, the space defined by each utility tray is substantially proportional to the number of elongated recesses. The utility tray or recess 20 or 22 is provided to hold the accessories normally used with syringes, such as small bottles, tape and cotton wool. FIG. 5 shows in dashed lines a syringe 24 to illustrate how it is engaged in an elongated recess 19 for its transportation. This is done by engagement of the capped needle 25 in the hole 23 with the opposite end of the syringe resting on the corresponding edge 13. The syringe is thus laterally restrained while being easy to grasp through its elevated portion. The cup-shaped recesses 21, as shown in FIGS. 1 and 2, serve to hold pills 26 to be dispensed to a patient.

A curved slot 27 is provided adjacent each recess 19 or 21 and it is provided to hold a card 28 to identify the patient meant to receive the injection or the pills. Indents 29 are spaced along the edge of the inner trays 17 and 18 in axial alignement with each pair of holes 15 and 16 to allow unhampered use of the latter to cap and uncap the needles of the syringes, as defined in the above-mentioned patent.

What I claim is:

1. A medical dispenser tray comprising an outer container defining a shallow cavity and an inner tray operatively resting into the shallow cavity, with the inner tray forming elongated recesses each having a hole in one end thereof, and being constructed and arranged for resting of a syringe therein with its capped needle in engagement in the corresponding hole, whereby the syringe will be retained in longitudinal position in the corresponding recess; wherein the outer container includes side walls, each of the elongated recesses is positioned adjacent one side side wall of the outer container and has the hole in said one end thereof positioned remote from said one side wall relative to the other end of the same recess, and each of the elongated recesses is constructed and arranged for engagement of a syringe therein with the latter having the opposite end relative to the needle extending over the correpsonding one side wall of the outer container.

2. A medical dispenser tray as defined in claim 1, wherein the inner tray constitutes a molded sheet having said recesses depressed therein, operatively resting on the bottom of the outer container and constructed and arranged to operatively support the inner tray in the shallow cavity of the outer container.

3. A medical dispenser tray as defined in claim 2, wherein the outer container includes a peripheral flange and is provided with pairs of holes spaced along the peripheral flange, each pair of holes includes one hole through the flange axially aligned downwardly inward with the second hole extending through a corresponding side of the outer container, and the inner tray includes indents spaced along the peripheral edge thereof in alignment with each pair of aligned holes.

4. A medical dispenser tray as defined in claim 3, wherein the inner tray includes a utility recess formed therein and constructed and arranged to place auxiliary treatment accessories therein.

5. A medical dispenser tray as defined in claim 4, wherein the elongated recesses are positioned in rows transversely across the inner tray and the utility recess extends in the same direction of said rows generally transversely co-extensive therewith.

6. A medical dispenser tray as defined in claim 5, wherein the inner tray includes cup-shaped recesses constructed and arranged to contain pills to be dispensed to patients, and a slot is provided in the inner tray adjacent each elongated recess and cup-shaped recess to insert a patient identification card therein.

* * * * *